Nov. 8, 1938. F MEILLAND Plant Pat. 303
ROSE
Filed Feb 28, 1938
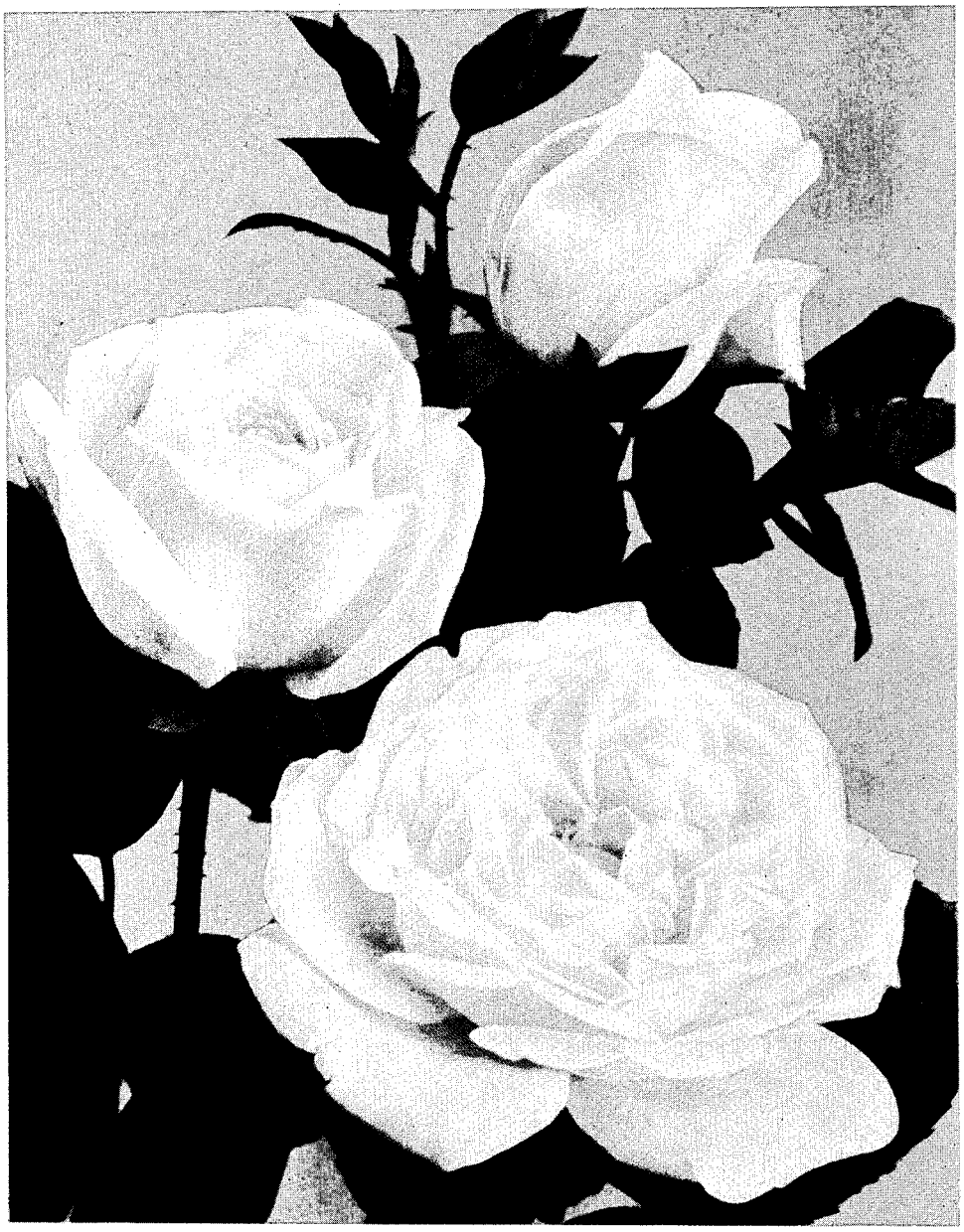
Inventor
Frances Meilland
By Robb & Robb
Attorneys Patented Nov. 8, 1938

Plant Pat. 303

UNITED STATES PATENT OFFICE

303

ROSE

Francis Meilland, Tassin-les-Lyon, France, assignor to The Conard-Pyle Company, West Grove, Pa.

Application February 28, 1938, Serial No. 193,165

1 Claim. (Cl. 47—61)

This invention relates to a new and distinct variety of rose plant and is the result of a definite effort to produce a rose in the yellow class possessing the desired characteristics of sturdiness of growth and depth of color and size of bloom, comparable to what has been produced in other color classes.

In carrying out the foregoing objective, I crossed the well known variety Charles P. Kilham with an unnamed seedling, and then the product of this cross, as the pollen parent, was crossed on Souv. de Claudius Pernet, as the seed-bearing parent.

The present rose resulting from the foregoing crossing is superior to any other yellow rose of which I am aware in its approach to the objectives hereinbefore referred to.

The dominating features of novelty of this new rose reside in the vigor of growth of the plant resulting in long, straight bloomstems bearing at the end flowers of a size and color that excel previous varieties. The color of the rose is unusually persistent in brilliant sunshine and for this reason the rose is one of great attractiveness.

This new variety has been asexually reproduced and the distinct characteristics herein set forth were transmitted true to form and appear to be permanently fixed.

The following is a detailed description of this new rose and its flower, all color designations being in accordance with the Ridgway Color Standard, except where the ordinary dictionary definition is obviously meant:—

Parentage:

*Seed parent.*—Souv. de Claudius Pernet.

*Pollen parent.*—Charles P. Kilham x unnamed seedling.

*Flower*

Blooming habit:

Continuous.

Bud:

*Size.*—1½ inches long.

*Form.*—Egg-shaped.

*Color.*—Lemon yellow.

*Sepals.*—Extra long, some up to 2¼ inches; width at base about ½ inch; light green on outside, light gray fuzz on inside. Some are pointed, others forming small leaves at tip; some have small leaflets on either side.

*Calyx.*—Urn-shaped.

*Peduncle.*—Strong; reddish green, lighter green toward the bud; rough.

*Opening.*—Opens well.

Bloom:

*Size.*—3 to 4 inches, in Pennsylvania.

*Borne.*—Erectly, singly.

*Stems.*—Long.

*Form.*—Loose form, inner petals cover center.

*Permanence.*—Lasting.

*Petalage.*—30 to 45 petals.

*Color.*—Lemon yellow.

Petals:

*Texture.*—Soft, smooth.

*Appearance.*—Soft.

*Form.*—Pear-shaped.

*Arrangement.*—Loosely formed.

*Persistence.*—Drop off cleanly.

*Fragrance.*—Fruity fragrance, suggestive of ripe apples.

*Lasting quality.*—Excellent.

Genital organs:

*Stamens, anthers.*—Average; color—Lemon with brown edge; arrangement—uneven.

*Stamens, filaments (threads).*—Uneven length; color—Some amber, others lemon.

*Pollen.*—Orange.

*Styles.*—Normal, uneven length.

*Stigmas.*—Normal and compact.

*Ovaries.*—Normal.

Fruit:

So far as I have been able to determine, the variety is sterile with its own pollen.

*Hips.*—None have appeared to date.

*Plant*

Form:

Bush.

Growth:

Upright, vigorous, long.

Foliage:

*Number of leaflets to compound leaf.*—1 on top of stem; 3 on second set from top; 5 on rest of leaves.

*Size.*—Medium.

*Quantity.*—Average.

*Color.*—Dark green.

*Shape.*—Oval.

*Texture.*—Leathery.

*Edge.*—Serrated.

*Serration.*—Uneven.

*Ribs and veins.*—Ordinary.

*Rachis.*—Color—light green; under side—Some smooth, others prickly.

*Stipules.*—Medium, bearded.

*Disease resistance.*—Not immune from blackspot.

Wood:

*New wood.*—Reddish green.

*Old wood.*—Reddish green.

Thorns:

*Quantity.*—Average.

*Form.*—Some slightly hooked, others straight.

*Color when young.*—red.

*Position.*—Irregular.

*Prickles.*—None.

*Short needles.*—none.

I claim:

A new and distinct variety of rose plant, characterized by its unusual vigor of growth, the straightness and sturdiness of bloom stem, combined with the abundant petalage, attractive form in all stages of development, and deep and lasting color of its blossoms, substantially as shown and described.

FRANCIS MEILLAND.